United States Patent [19]
Ylvisaker

[11] Patent Number: 5,361,625
[45] Date of Patent: Nov. 8, 1994

[54] METHOD AND DEVICE FOR THE MEASUREMENT OF BARRIER PROPERTIES OF FILMS AGAINST GASES

[76] Inventor: Jon A. Ylvisaker, Rt. 1, Box 109, Zumbro Falls, Minn. 55991

[21] Appl. No.: 54,691

[22] Filed: Apr. 29, 1993

[51] Int. Cl.$^5$ ............................................. G01N 15/08
[52] U.S. Cl. ....................................................... 73/38
[58] Field of Search ...................... 73/38, 19.05, 19.06

[56] References Cited

U.S. PATENT DOCUMENTS

| | | | |
|---|---|---|---|
| 3,604,746 | 9/1971 | Toren | 73/38 |
| 3,902,068 | 8/1975 | Wood | 250/343 |
| 3,926,561 | 12/1975 | Lucero | 73/38 |
| 4,656,865 | 4/1987 | Callan | 73/38 |
| 5,081,863 | 1/1992 | Reid | 73/38 |
| 5,107,696 | 4/1992 | Mayer et al. | 73/38 |

OTHER PUBLICATIONS

DeLassus et al. "Transport of Apple Aroma in Polymer Films" Food and Packaging Interactions, ACS Symposium Series, No. 365, 1988, pp. 11-27.
Gilbert et al. "Find new . . . ", Package engineering, 14(1), 1969, pp. 66-69.
Hernandez et al. "Measuring the Aroma Barrier Properties . . . ", Packaging Technology, Jul./Aug. 1986, pp. 12-15.
DeLassus, "Determining the Permeabilities, Diffusivities, and Solubility, etc." 1986 Polymers, Laminations, etc. pp. 333-337.
Landois-Garza et al, "Permeation of High-Barrier Films by Ethyl Esters", Chapt 4 Food and Packaging interactions, ACS 1988.
Meigh, D. F., "A Solid State Amplifier for the Flame . . . " Journal of Physics E (Scientific Inst.) vol. 4, No. 1 pp. 66-68, Jan. 1971.
DeLassus, et al., "Flavor and aroma permeation in . . . " TAPPI Journal, Nov. 1988, pp. 177-181.
Ziegel, et al., "Measurement of Hydrogen Isotope Transport . . . " J. of Polymer Sci., part A-2 vol. 7, 809-819 (1969).
Landois-Garza, et al., "Permeation of High Barrier Films . . . " Food and Packaging Interactions, ACS 1988 pp. 42-58.
Glacin, et al., "Evaluation of the Aroma Barrier Properties . . . " Activities and report of the R&D Associates, Mich. St. Univ. vol. 39 No. 1, 1987 pp. 79-90.
Gilbert, et al., "Find new way to measure gas permeability" Package Engineering, 14(1) 1969 pp. 66-69.
Felder, et al., "Permeation, Diffusion, and Sorption of Gases . . . " Methods of Experimental Physics, vol. 16c (1980) pp. 315-377.
Baner, et al., "Isostatic and Quasi-Isostatic Methods for Determining the Permeabiity of Organic Vapors Through Barrier Membranes", Symposium on Current Technologies in Flexible Packaging, Nov. 1, 1984.
Hatzidmitria, et al., "Odor Barrier Properties of Multi--Layer . . . " J. Food Sci, vol. 52 (2) pp. 472-474 1987.
Zobel, "The Odour Permeability of Polypropylene . . . " Polymer Testing, vol. 5 1985 pp. 153-165.

*Primary Examiner*—Hezron E. Williams
*Assistant Examiner*—Michael J. Brock
*Attorney, Agent, or Firm*—Dennis H. Rainear

[57] ABSTRACT

The present invention is directed to a novel apparatus for measuring the transmission or permeation of gases, flavors, aromas and volatile substances through films and membranes. The instrument of the present invention also provides the capability of high rate testing in order to allow the expedient analysis of multiple film samples within a reasonable amount of time. This invention also provides an instrument and method for extremely high sampling rate of permeant gas with little or no background noise, whereby detection sensitivity is greatly enhanced relative to conventional testing instruments.

6 Claims, 6 Drawing Sheets

METHOD AND DEVICE FOR THE MEASUREMENT OF BARRIER PROPERTIES OF FILMS AGAINST GASES

TECHNICAL FIELD

The invention relates to a device for the measurement of barrier properties of films, such as packaging materials.

BACKGROUND ART

The conventional method for measuring the barrier properties of films consists of placing a film sample between two chambers containing a test gas of interest in a first chamber and a carrier gas in the second chamber. As the test gas permeates through the film sample, it is collected in the second side and subsequently measured by an appropriate detector. Initially, the measured value of detected test gas will be near zero if the test chambers have been thoroughly flushed of the gas being measured. Over time, the detector response value will increase until it reaches a point of equilibrium, often referred to as the steady state value. This steady state value is then used to define the film material's barrier property in terms of a rate of permeant transmission per unit time per area of measurement. Other factors which contribute to the measurement value are often referenced and include the film thickness, the measurement temperature, relative humidity, and other specifics of the test gas mixture, such as ratios of other gases present.

The relationship among permeability, solubility, and diffusion of the permeant or test gas is normally described by a direct proportionality: $P = DS$, where P is the permeability coefficient, S is the solubility coefficient, and D refers to the diffusion coefficient. If two of these coefficients are known, the other may be calculated directly. It is apparent, therefore, that an instrument designed to evaluate film protection properties should provide the means to determine at least two of the above coefficients.

Several permeation measurement methods have been described in the literature. The three most common methods include a gravimetric technique, an integrating technique, and a derivative technique. The derivative technique employs a direct measurement of the film permeation value, and since it provides information regarding the transient permeation properties as well as the steady state conditions, this method may also be used to evaluate solubility and diffusion rate values. It is also the method which is most representative of actual end use conditions of the film since the method provides the analysis of permeation from a high concentration to a near zero concentration. However, since the derivative method does not employ a concentration of the measured gas, extremely low senitivities are required, typically on the order of parts per billion. However, such sensitivity has been unobtainable due to the presence of excessive background signal noise which blocks the sensitive readings. It would therefore be of value to the industries involved with materials barrier analysis to have an instrument capable of achieving low sensitivity measurement.

U.S. Pat. No. 5,081,863, issued Jan. 21, 1992 to Reid, teaches an apparatus with multiple test cells for measuring gas transmission through films. The preferred detector of the device of Reid uses a thermal conductivity cell, which is a detector known to be sensitive to temperature changes. This, as well as the multiple cells of Reid, prevents the adequate measurment of a material's barrier performance in the initial stages of transmission, the transition state where signal strength is small.

U.S. Pat. No. 3,902,068, issued Aug. 26, 1975 to Wood, teaches a method of detecting the passage of a gas through a barrier by measuring the variance or modulation of radiant energy transmitted through compressed gas which has passed through the barrier. The presence of modulation of the radiant energy transmitted is indicative of gas passage through the barrier.

U.S. Pat. No. 5,107,696, issued Apr. 28, 1992 to Mayer et at., teaches a system for measuring gas permeability of membranes by using a metallic block possessing exceedingly good heat transfer characteristics which becomes a precisely controlled heat sink for the entire system.

BRIEF DISCLOSURE OF INVENTION

It is the principal object of this invention to provide a novel apparatus for measuring the transmission or permeation of gases, flavors, aromas and volatile substances through films and membranes.

It is a further object of the present invention to provide an instrument with the capability of high rate testing in order to allow the expedient analysis of multiple film samples within a reasonable amount of time.

It is a still further object of this invention to provide instrumentation for adequate comparison or correlation of detector response levels with temperature values.

Yet another object of this invention is to provide an instrument and method for extremely high sampling rate of permeant gas with little or no background noise, whereby detection sensitivity is greatly enhanced relative to conventional testing instruments.

Two significant components of the present invention include (1) a unique flow control system, and (2) improved data logging or sampling rate. Thus, by the present invention, column end fittings are used as the flow rate control system, similar to that normally utilized in a gas chromatograph column, instead of conventional flow meters or needle valves commonly used in film barrier testing instruments. Such column end fittings, as further described herein, have not been previously used in devices for measuring the permeation of vapors through film barriers.

In addition, prior art sampling rates are on the order of one sample per second. However, by the present invention, 1000 to 4000 samples per second are easily obtained for each data point by means of employing an analog to digital converter installed in or connected to a computer connected to the gas detector. This dramatic increase in the sampling rate, in conjunction with the above-mentioned flow rate controls, allows the reduction of the background noise to levels previously unobtainable. In this manner, the present invention provides an instrument with a sensitivity which is significantly enhanced over the instruments or measuring devices of the prior art.

The foregoing, as well as other objects and advantages of the present invention, will become apparent from the following specification and claims, and with reference to the Figures.

BRIEF DESCRIPTION OF FIGURES

In describing the preferred embodiment of the invention which is illustrated in the figures, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

Figure 1:
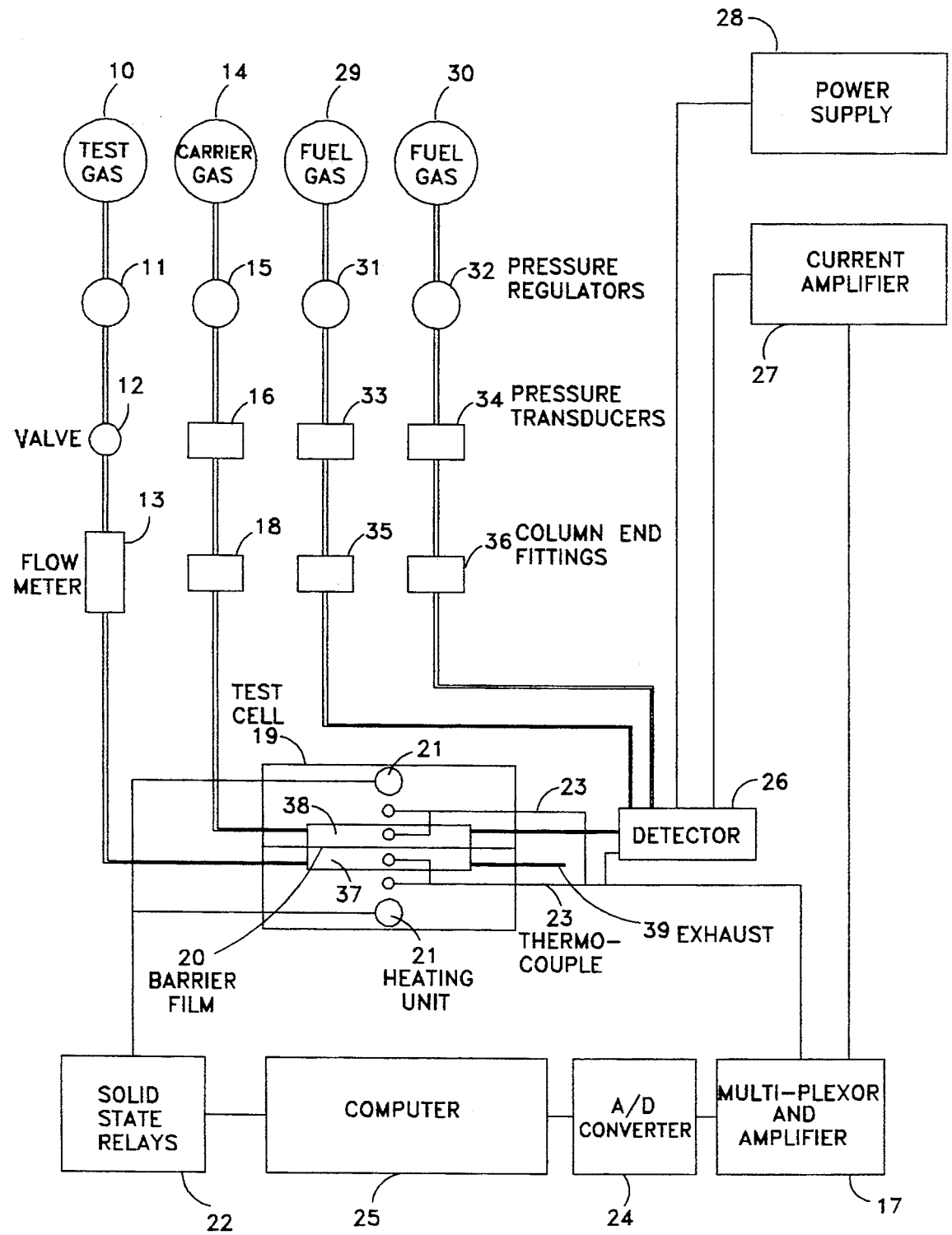
FIG. 1 illustrates a schematic lay-out of one embodiment of the present invention.

The present invention relates to an instrument for the analysis of vapor transmission through film or barrier materials. This is particularly useful in the testing of, for example, film materials used for the packaging of foods, medicines, and other materials sensitive to contamination.

In one embodiment of the present invention, an instrument is provided which comprises a test cell containing the film sample being tested, a detector for the measurement of permeant vapor concentrations, a means to control test gas flow rates, and a means to record temperature and detector response values.

Thus in one embodiment the present invention is directed to an apparatus for detecting the passage of gas through a barrier film, said apparatus comprising;

a) an organic barrier film;

b) a test cell for holding the film, whereby the test cell is divided into a first side and a second side by said barrier film;

c) a means for supplying a test gas flow to the first side of the test cell;

d) a means for supplying a carrier gas to the second side of the test cell;

e) a detector for measuring test gas concentrations on said second side of the test cell, said detector able to send an analog output signal, wherein said output signal is proportional to the test gas concentration detected; and f) a computer to receive the output signal from the detector, convert the analog signal to a digital signal, and average the signals, whereby the apparatus is able to measure the permeant gas concentration at a sensitivity level and speed not available in the prior art devices. Additionally, but not required, a means to record the gas temperature, pressure and flow rate of the test gas, is useful herein when attached to the apparatus described above.

The present invention also relates to a method of detecting the passage of gas through a barrier film comprising the steps of;

a) exposing a first side of a barrier film to a test gas, whereby the test gas can permeate through the barrier film forming thereby a permeant gas;

b) exposing a second side of the barrier film to a carrier gas which mixes with the permeant gas;

c) collecting the carrier gas and permeant gas mixture in a detector able to detect the concentration of the permeant gas, whereby the detector can produce an analog signal which is proportional to the permeant gas concentration detected;

d) converting the analog signal from the detector to a digital signal; and e) averaging a plurality of digital signals.

In a preferred embodiment of the present invention, the detector is a flame ionization detector. An example of a useful flame ionization detector useful herein, and not by way of limitation, is the Model 12-800 flame ionization detector available from Gowmac, Inc, of Bound Brook, N.J. This flame ionization detector consists of a flow means and flow tip, a repeller, and a collector, inlets for hydrogen, air and a test gas, an ignition plug and a stainless steel encasing. This detector generates an output analog signal proportional to the concentration of permeant gas detected. For the Model 12-800 flame ionization detector at a carrier flow rate of 35 milliliters per minute, a 1 ppm concentration of ethanol will yield a current signal of approximately 3 pico amperes. As the signal noise of this detector is on the order of 1 picoampere, the sensitivity of the instrument is on the order of 1 ppm. Other known gas detectors are also useful herein, perferably those which also can produce an output analog signal.

In this embodiment or a separate embodiment, a recording means then records response values at a rate of at least 1000 Hz.

Incorporation of the above elements and principles described herein allow vapor or permeant gas detection levels in the parts per billion range, and allow the precise measurement of the transmission rate transient properties as well as the steady state values. Prior art devices have avoided direct measurements of the permeant gas concentration because the concentration is so low as to be undetectable, or at least excessively obstructed by signal noise levels. However, by the present invention, the actual gas levels are directly detectable without unacceptable signal noise levels because of the averaging of up to 4,000 signals per second.

Further, by the present invention the actual gas concentration detected is so close to the theoretical values according to Fick's Law, that one can predict equilibrium points long before equilibrium occurs by merely having a few early points to establish the initial response curve. Then simple calculations allow the interpolation or extrapolation needed to predict the values at any later point in time. This feature of the present invention is demonstrated in FIG. 5 which, in fact, depicts both the actual analog signal levels detected vs. time, as well as the theoretical values vs. time. It can be readily seen from FIG. 5 that the device of the present invention generates an actual curve virtually identical to, and superimposed upon, the theoretical curve. This illustrates the ability of the devices of the present invention to accurately and directly measure the gas levels at very low concentrations without obstructive signal noise. The analog signals are then converted to digital signals and averaged as described herein.

By "film" or "barrier film" herein is meant any organic film, membrane, sheet, or the like, which can be a monomer, polymer, copolymer, terpolymer, composite or laminate multi-ply structure, rubber, plastic, mixture thereof or blend thereof. While the applicable films herein are flexible packaging films, other useful barrier films herein can include semi-flexible, semi-rigid, or rigid packaging materials which might be used to contain, retain, or exclude a test gas. Such films can include by example and not by limitation polyvinyl chloride, polyvinylidene chloride, acrylics or polyacrylates, polyesters, polycarbonates, polyamides, natural rubber, butadiene rubber, styrene, polystyrene, and copolymers, mixtures, or laminates thereof.

By "test gas" herein is meant any organic or inorganic vapor, flavor, aroma, gas, mist, smell, or the like which is capable of detection by the detector of choice. The applicable vapors or test gases for a flame ionization detector are organic vapors. Examples of organic vapors detectable by the present invention can include, and not by limitation herein, ketones, aldehydes, esters, ethers, amides, amines, alkanes, alkenes, alkyl halides, sulfonates, phenols, heterocyclic hydrocarbons, mercaptans and thiols, carboxylic acids, alcohols, glycols, polynuclear aromatic compounds and the like, and mixtures thereof and derivatives thereof which are in the vapor state or can become vaporous under the test conditions of varied temperature and pressure. Inorganic vapors generally require a detector system other than flame ionization detectors, such as thermal conductivity detectors, mass spectrometers, or infrared detectors. Examples of inorganic vapors detectable by the present invention can include, for example and not by limitation, water vapor, hydrogen sulfide, hydrogen cyanide, hydrochloric acid, nitrogen, carbon dioxide, carbon monoxide, sulfur dioxide, helium, neon, argon, krypton, xenon, fluorine, chlorine, bromine, oxygen, hydrogen, and the like and mixtures thereof.

By "permeant" herein is meant the test gas or gases after permeation through the barrier film. The permeant gas is then mixed with and swept by the carrier gas through the second side or chamber of the test cell and to the detector.

In one utilization of the present invention, the test gas being detected is one which evolves or is liberated from a food or other commodity which can be packaged in the barrier film being tested. Similarly, the testing of the film can measure permeation of the external gases in the immediate environment which might penetrate the packaging and introduce contamination or flavor degradation into the packaged product, such as a food, medicine, medical or sterile device.

By "carrier gas" herein is meant any inert gas useful as a carrier or blowing gas to sweep or convey the test gas which has permeated the film onto the detection system. The preferred carrier gases herein are non-carbon containing since carbon is detected in the flame ionization detector which would therefore necessitate a calculation to yield a net result based on the permeant or test gas alone. Examples of effective carrier gases herein include, for example, nitrogen, argon, helium, and air, but other non-carbon carrier gases can be used. Flame ionization detectors generally use a mixture of fuel gases, such as hydrogen and air. FIG. 1 shows these fuel gases being fed into the detector through pressure regulators, pressure transducers, and column end fittings.

According to the present invention, a test gas of interest is metered into a first side or portion of a test cell cavity which is partitioned into a first chamber or side and a second chamber or side by the barrier film sample to be tested. A carrier gas, such as argon, air, helium or nitrogen, is then transmitted into the second side of the test cell, i.e., on the side of the film sample opposite the test gas. The second portion of the test cell cavity is connected to a gas detector, preferably if the gas to be measured is organic, a flame ionization detector. Thermocouples are mounted in the walls of the test cell cavity for detection and proper maintenance of test cell temperature, and additionally in the cell cavity to obtain precise measurement of the test gas temperatures. The thermocouples are connected to heat generators or heat sources which can introduce sufficient heat with sufficient control to facilitate accurate and constant temperature attainment and retention. The heat sources can include, for example, devices such as cartridge heaters, band heaters, strip or cable heaters, or tube heaters. The preferred heat sources herein are fire rod cartridge heaters, such as those obtained from Watlow Electric Co., St. Louis, Mo., but other heat sources known in the art are useful herein.

As molecules of the test gas permeate through the barrier film from the first portion of the test cell into the second portion to thereby form the permeant, they are swept by the carrier gas stream within the second portion through the detector system and subsequently measured. Since the detector response is proportional to the concentration of permeant gas or gases, the resulting current analog signal output from the detector yields a value which is proportional to, and thereby indicative of, the molecular transfer of test gas across the film being tested.

Gas flow rates into the test cell are controlled in the present invention by a combination of double stage pressure regulators and column end fittings with sintered metallic frits. The preferred metal for the frits is steel, however other metals can be used to form the frits useful herein. Steel frits useful herein include, for example, those available from Swagelok Company, Solon, Ohio. The frits preferably contain micron sized pores which restrict the flow of gases to a level which is usable by the dectector system. This level is generally from about 20 to 30 mililiters per minute for hydrogen, 280 to 320 mililiters per minute for air, 20 to 40 mililiters per minute for a carrier gas, and 20 to 100 mililiters per minute for the test gas. These gas flow levels are not limitations and are provided as perferred embodiments only.

The precise rate of flow is then controlled by the pressure of each respective gas on the front side of its corresponding frit and this pressure is measured by a pressure transducer or by a direct reading of a pressure regulator. The pressure transducers useful herein can include those available from Sensotec, Columbus, Ohio. The pressure tranducers are located between the pressure regulator and the column end fitting of each respective gas. In conjunction, the pressure regulator is located between the gas supply source and the column end fitting, and can be of the R-77 series as supplied by L-TEC.

Of the details shown in FIG. 1, two important factors to the sensitivity of the present invention include (1) the means to control gas flow rates and temperature, and (2) the means to sample the flame ionization detector at a high sampling rate. Temperature and flow rate are critical because of their relationship to a molecular concentration level within the detector. This relationship is well known and is often referred to as the Ideal Gas Law; $PV=nRT$, wherein P is the pressure of the gas, V is the volume occupied by the gas, R is the ideal gas constant, T is the gas temperature and, n is the number of molecules. The concentration of a gas in molecules per unit volume is therefore: $n/V = P/RT$. Thus, the concentration is directly proportional to pressure and inversely proportional to the temperature. Slight variations in these quantities will have a direct effect on the concentration of the gas being measured. It is therefore apparent that control of these quantities is critical to the measurement or calculation of a permeant gas concentration.

The control of temperature is well known in the art. Factors which dictate the degree of control achieved include the geometry of the component to be controlled as well as the precision with which the component temperature may be measured. Preferably, geometry variations are minimized by reducing the number of components within the system. Elimination of system valves and transfer lines is certainly a means of achieving that end, and it is therefore apparent that the highest degree of control will be achieved with a single cell system. Thus by the present invention, the measurement of system temperature is improved by a simplification of the system geometry by limiting the number of test measurement cells to one.

As shown in FIG. 1, cell temperature is evaluated by a series of thermocouples connected to a multiplexor/amplifier which is in turn fed to an analog-to-digital converter and computer system. As in the case with any electrical device, a thermocouple transducer signal will contain some background noise. This noise detracts from the precision of the measurement, and by conventional methods would not provide sufficient information for the precise temperature control required. However, by the present invention, the signals are transferred to a computer system and the measurements may be averaged until sufficient precision is achieved. An averaging of 10 to 50 measurements has been shown to be adequate with the system disclosed herein, but 10–50 measurements is not a limitation of the present invention, and in fact, sampling numbers as high as 100 are useful herein. The aforementioned averaging may be accomplished according to the present invention within a time span on the order of a millisecond.

As discussed above, the control of test gas system flow rates is as critical as is temperature control. Again, simplification of the system design is a factor, and the employment of a single cell system is used herein, as opposed to conventional multiple cells, as a means to achieve that simplification.

FIG. 1 shows the general layout of the preferred embodiment of the present invention. The test gas to be measured, as well as the carrier gas such as nitrogen is connected to the test cell chamber through a two stage pressure regulator, as well as a column end fitting. The column end fittings act as a converter, i.e., it converts a pressure value to a flow rate value through it's action as a flow rate control and offers the additional advantage of providing a convenient means of measuring the system flow rate. FIG. 1 shows the means to accomplish that measurement and comprises a pressure transducer mounted between the pressure regulator and the column end fitting.

FIG. 1 shows the several components of the apparatus of the present invention. The test gas supply source 10 is connected to a pressure regulator 11 which feeds the test gas at a desired rate through a metering valve 12 to the flow meter 13. Similarly, the carrier gas or gases, including for example, nitrogen, hydrogen, air or mixtures thereof, can be fed from the supply source 14, through the pressure regulator is into the pressure tranducer 16. The pressure transducer 16 is connected to and interpreted by the multiplexor and amplifier 17. The carrier gas or gases which exit the pressure transducer 16 pass into the column end fitting 18 which contains the metallic frit able to control and achieve the desired flow rate. The test gas and the carrier gas then enter the test cell 19 on either side respectively of the barrier film 20. The test cell 19 is also equipped with heating units 21 connected to solid state relays 22 useful as temperature controllers. Both the test gas side 37 and the carrier gas side 38 of the test cell are equipped with thermocouples 23 able to detect the temperature of the test cell environment and relay this information to the multiplexor and amplifier 17. Test gas side 37 of the cell 19 has an exit or exhaust port 39. The multiplexor and amplifier 17 is connected to a computer 25 through an analog-to-digital converter 24. The computer 25 can send to the solid state relays 22 an electronic signal indicative of the temperature detected by the thermocouples 23, whereupon the heating units 21 can be activated or deactivated to thereby attain or maintain a desired temperature. The test cell 19 is connected to a detector 26, such as a flame ionization detector, which receives the mixture of permeant gas and carrier gas. The detector 26 is connected to a current amplifier 27. The current amplifier 27 is also connected to the multiplexor and amplifier 17 to thereby obtain signal amplification. The detector 26 also is connected to a power supply 28. When the detector used is a flame ionization detector, it is preferably connected to fuel gas supplies, 29 and 30, including hydrogen and air. The fuel gas supplies are connected to pressure regulators 31 and 32 and pressure transducers 33 and 34. Each fuel gas supply line has a column end fitting 35 and 36, which include porous metallic frits. The schematic diagram of FIG. 1 is not a limitation in the present invention and similar, related and derivative assemblies are also within the scope of the present invention.

The precision achieved in the flow rate control of the present invention is novel and unexpected in view of the control attained by conventional devices using fine metering valves. This improvement is due predominantly but not exclusively to a buffering of the pressure difference across the column end fitting and is effected by, for example, a sintered steel frit, which consists of a porous steel disk. The pores in the disk are preferably on the order of a micron in diameter but may range from about 0.1 to 25 microns in diameter. When a pore size of 1 micron is used herein, a flow rate of from 20 to 40 milliliters per minute is achieved at a pressure difference across the frit of 40 psi. Preferred column end fittings with sintered steel frits may be obtained from Swagelock Inc., Solon, Ohio.

Although the relationship between pressure difference and flow rate is not linear, it is a predictable relationship which may be precisely calibrated for a specific gas. By the present invention, the flow rate values achieved are proportional to the square of the pressure difference across the frit, are highly stable over significant periods of time, and are unaffected by normal temperature changes within the system.

Since the pressure difference may be directly fed to a computer system through a pressure transducer and an analog-to-digital converter, the use of a squared relationship to define the actual gas flow is not an issue. The necessary calculations are easily accomplished within the computer and the logging of flow rate data into computer files for documentation purposes is effected simultaneously.

The sampling rate of the devices of the present invention is on the order of up to, for example, 4000 samples per second per data point. The sampling rate, however, can be higher or lower, and is preferably in the range of 1000 to 4000 sample measurements per second for each data point. This enhanced sampling is achieved in the present invention by means of an analog to digital converter interfaced to a central processing unit. The analog-to-digital converter could be part of an input/output subsystem, or contained within a microcontroller or microprocessor. Examples of such an analog-to-digital converter can include, but not as a limitation herein, ADC 0808, available from Analog Devices. The extremely high sampling rate relative to conventional sampling systems provides herein an ability to average the many samples per data point without increased background noise. This dramatic increase in sampling rate without a corresponding increase in background noise results in greatly enhanced sensitivity in the testing devices of the present invention, relative to the instruments of the prior art. The preferred system will incorporate a computer interface to allow a sampling of the detector signal at a rate sufficiently high to allow a smoothing of the signal to a level consistent with the degree of precision obtained in the temperature and flow rate control. By the present invention, a sampling of at least 1000 measurements is required, and a sampling rate of as high as, for example, 4000 measurements yields exceptional results.

The output current or signal from the detector, preferably a flame ionization detector, is amplified by means of a current amplifier and the signal is passed on to a computer system through a multiplexer and an analog to digital converter. The multiplexer can be a board such as the CIO-EXP 16, supplied by Computer Boards Inc. of Mansfield, Mass. No signal results into the computer from argon, helium or nitrogen carrier gas, if a flame ionization detector is used because the flame ionization detector detects carbon compounds, so the net signal from the detector to the computer is due to the permeant gas. The multiplexer also receives the input signals from the pressure tranducers and the thermocouples. The multiplexer then queues the signals to the analog-to-digital converter. In combination, these signals provide all of the critical operating and measurement parameters necessary to anaylze the barrier film sample, including test gas concentration, test gas temperature, and system flow rate control, since the volume and gas constant (R) remain unchanged.

This information can be used as raw data, or further processed in the computer within a program designed to interpret, analyze, process or otherwise manipulate the information to produce a desired format.

Optionally, the test cell in the present invention can also be connected to a gas chromatograph (GC) and a mass spectrometer (MS). The GC separates the gases in a mixture into individual gases based on retention time on or through packed columns or tubes. The effluent from the GC can be fed to a MS for identification of the particular gas or gases. In this manner, the present invention can not only test the permeability of the barrier film sample, but also identify the gas or gases which are most readily transmitted through the film being tested. In addition, the relative permeability or transmissivity of the film against classes or molecular weights of volatile gases or vapors can be determined. Also, relative rates of permeation over time can be determined by this invention to thereby compare various gases.

In addition to the readout of the operating parameters and the transmission measurement value, the computer used in the present invention controls the temperature settings of the test cell and the detector through one or more temperature controllers. This allows the operator to vary the test conditions to evaluate a film's potential use as a food packaging material in different temperature environments.

Measurement of gas permeability through membranes requires sensitive gas detectors since the quantities of measured gas are frequently quite low. It is therefore important that the entire system involved in such measurments be maintained under tightly sealed conditions, particularly with respect to all of the gas flow passages leading to the gas detector. It is desirable that in the devices of the present invention the cell portion containing or associated with the flame ionization detector is fitted with a means, such as, but not limited to an "O" ring to assure minimal leakage and all connectors to the gas streams incorporate pressure fit stainless steel fittings with "O" rings. The preferred "O" rings herein are made of a plastic or rubber able to tightly seal and deform around a fitting. The preferred plastic material useful herein for the "O" rings is a fluorocarbon elastomer, such as Viton, but other materials known in the art are also useful herein.

The device of the present invention can include a means to record the data compiled by the computer in receiving the temperature signals, flow rate signals, and pressure signals. The recording means can include, for example, a computer memory bank or hard disc, a printer or strip chart recorder on which is produced by the present invention a plot or graph typical of a diffusion reaction. When measurements are conducted at a number of temperatures, an Arrhenius plot of the change in the log of the permeability versus the inverse of the temperature may be constructed. This produces a linear relationship which is not new and is known to those skilled in the art, but with a degree of sensitivity not heretofore obtained.

Thus, by the present invention, one can readily measure permeation values at a high test temperature and then extrapolate to a lower temperature more representative of the intended use conditions for the film being tested, or vice versa. Since this relationship between the change in the log of the film permeability and the inverse of the temperature is linear, extrapolating becomes a straightforward procedure, and offers a significant improvement over the art. In fact, by the present invention the extrapolation from one temperature to a second temperature along the linear graph can be performed readily by the computer to yield a direct permeability measurement result at any desired second temperature, or series of temperatures.

Figure 2:
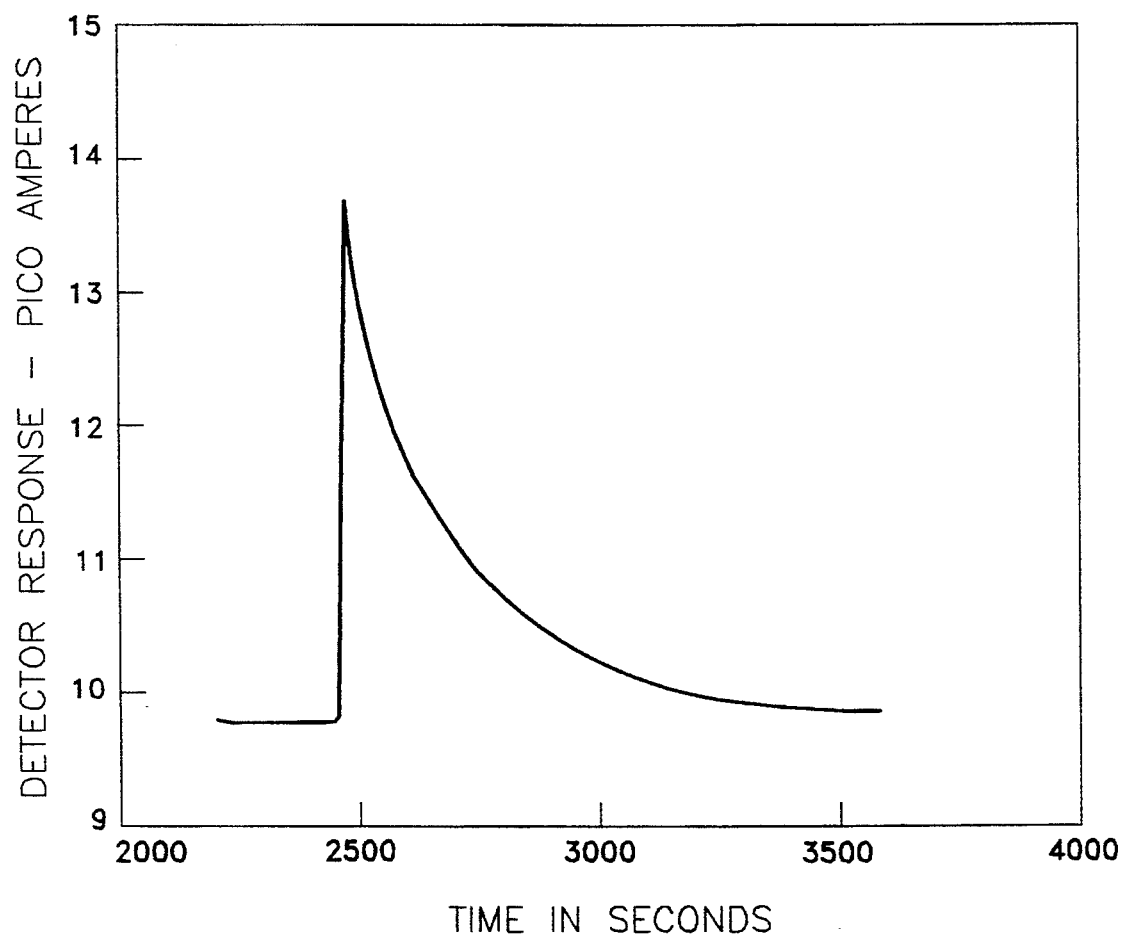
FIG. 2 illustrates a graph of the flame ionization detector response, measured as amps vs. time, of a 10 microliter injection of ethanol vapor into the detector side of a device of the present invention.

FIG. 2 illustrates a curve representing the flame ionization detector response in picoamps vs. time measured in thousand seconds. The picoamps measurement of the y-axis is a current measured out of the detector and is the analog signal. The graph shows the response of the device of the present invention to the direct injection of 10 microliters of ethanol directly into the test cell without permeation; i.e., no film barrier was employed. Excessive signal noise would be evident by a much more jagged and erratic line on this Figure. This Figure was prepared for calibration purposes. In performing the test which produced FIG. 2, the following values were employed:

cell dimensions (inches)
 diameter: 4.0
 depth: 0.75
cell volume (cu. in.): 9.42
cell volume (cc): 154.3661428
injection volume (microliters): 10
percent alcohol: 47.3
vapor pressure of ethanol (mm Hg): 49
injection
 ethanol fraction: 0.030496052
 volume fraction: 0.000064781
 total fraction: 0.000001975
total fraction in ppm: 1.975566148

FIG. 2 thus demonstrates the high sensitivity of the present invention in the parts per million range above, and as evidenced by the very smooth nature of the line.

Figure 3:
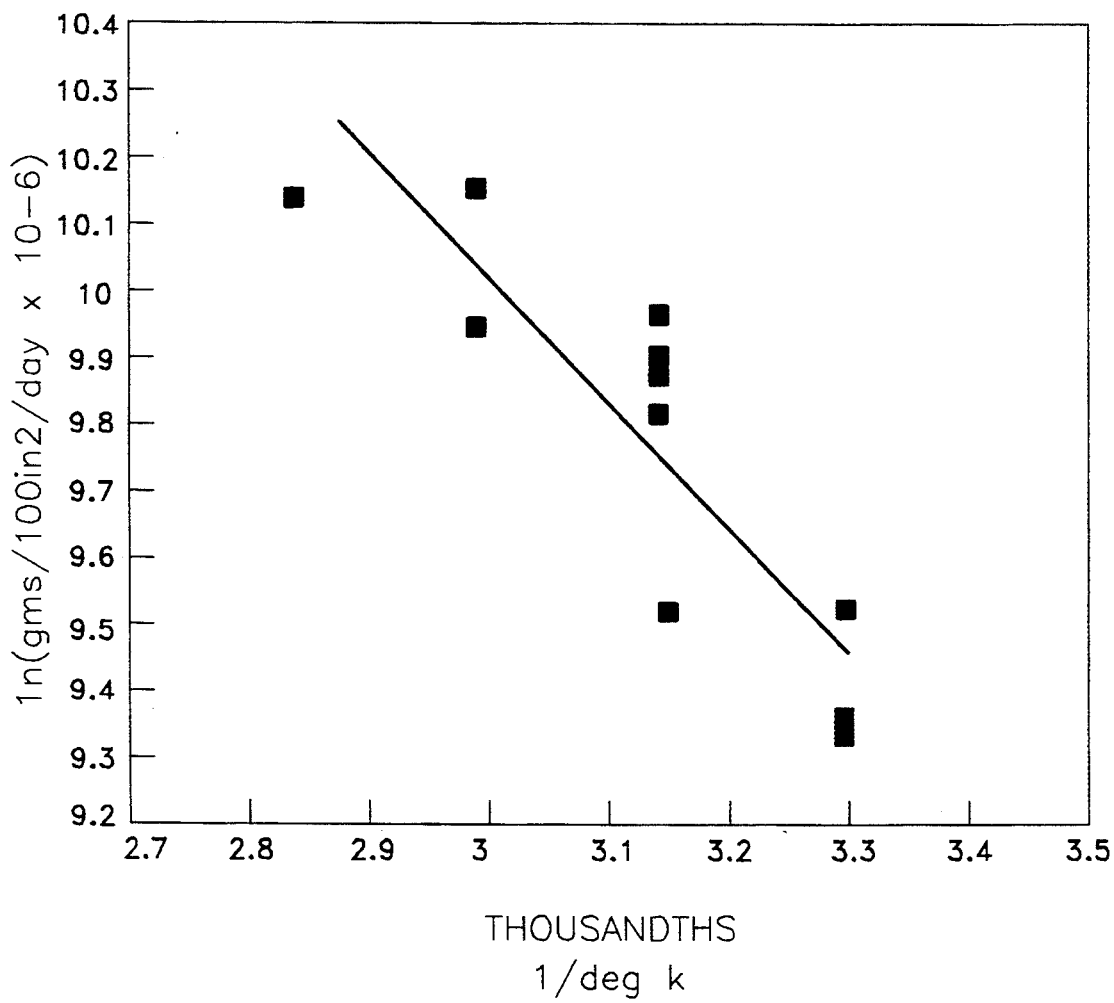
FIG. 3 illustrates an Arrhenius plot of high density polyethylene film permeation rate according to the present invention.
Figure 4:
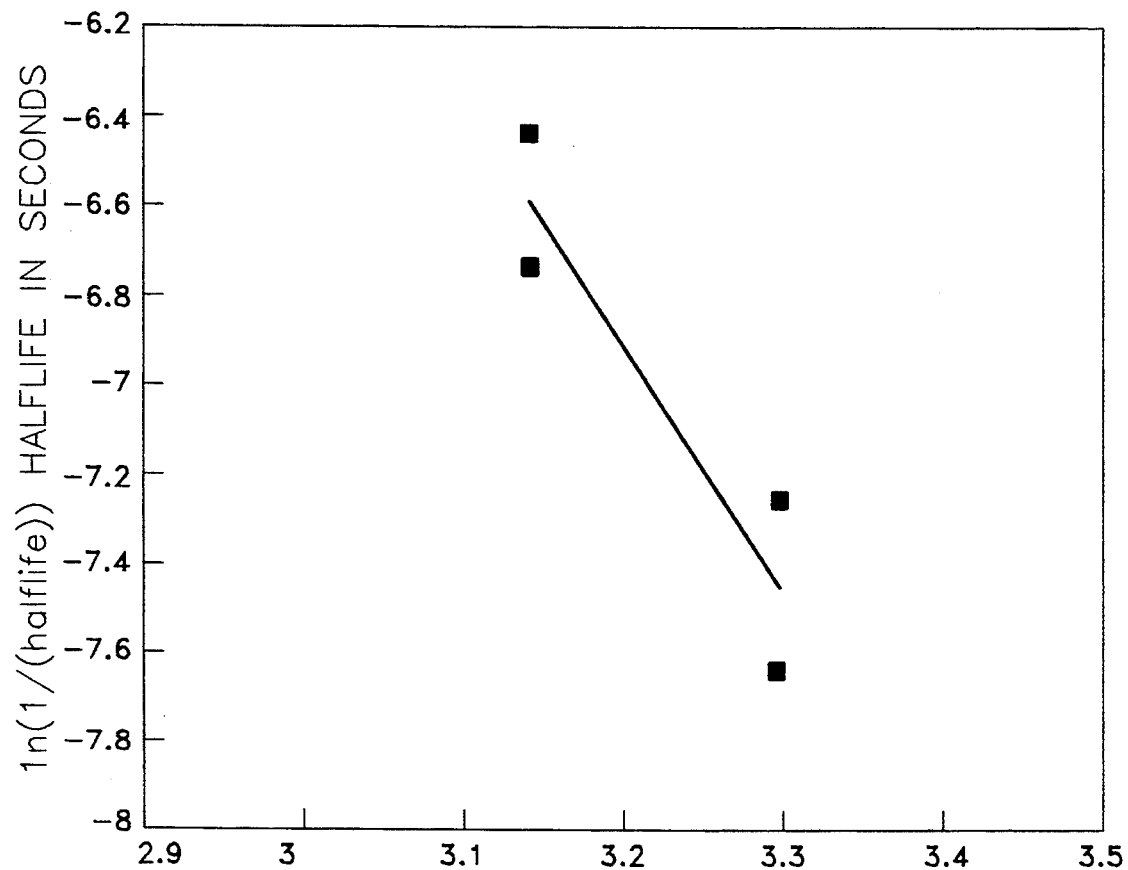
FIG. 4 illustrates an Arrhenius plot of diffusion measured by the present invention through high density polyethylene film.

FIG. 3 illustrates an Arrhenius plot of permeability vs. inverse temperature. The data of FIG. 3 is the natural log of the measured permeation rates of D-limonene at 100 ppm through 1.5 mil thick high density polyethylene film versus the inverse temperature in degrees Kelvin. The line is the average of the observed values. This Figure, as well as FIG. 4, illustrates the use of the relationship between permeation and diffusion vs. temperature to extrapolate to low temperature or room temperature values, whereby the present invention can predict accurately the expected permeation values. The advantage of this is in test throughput, as elevated temperatures significantly increase the molecular diffusion rates.

FIG. 4 is an Arrhenius plot of test rate vs. inverse temperature. The data represent the natural log of the permeation half life versus the inverse of temperature. The Figure illustrates the data from the diffusion of D-limonene at 100 ppm through high density polyethylene as detected by the present invention. Diffusion is equal to permeation divided by solubility. The half life of the permeation experiment is inversely proportional to the material diffusion rate.

Figure 5:
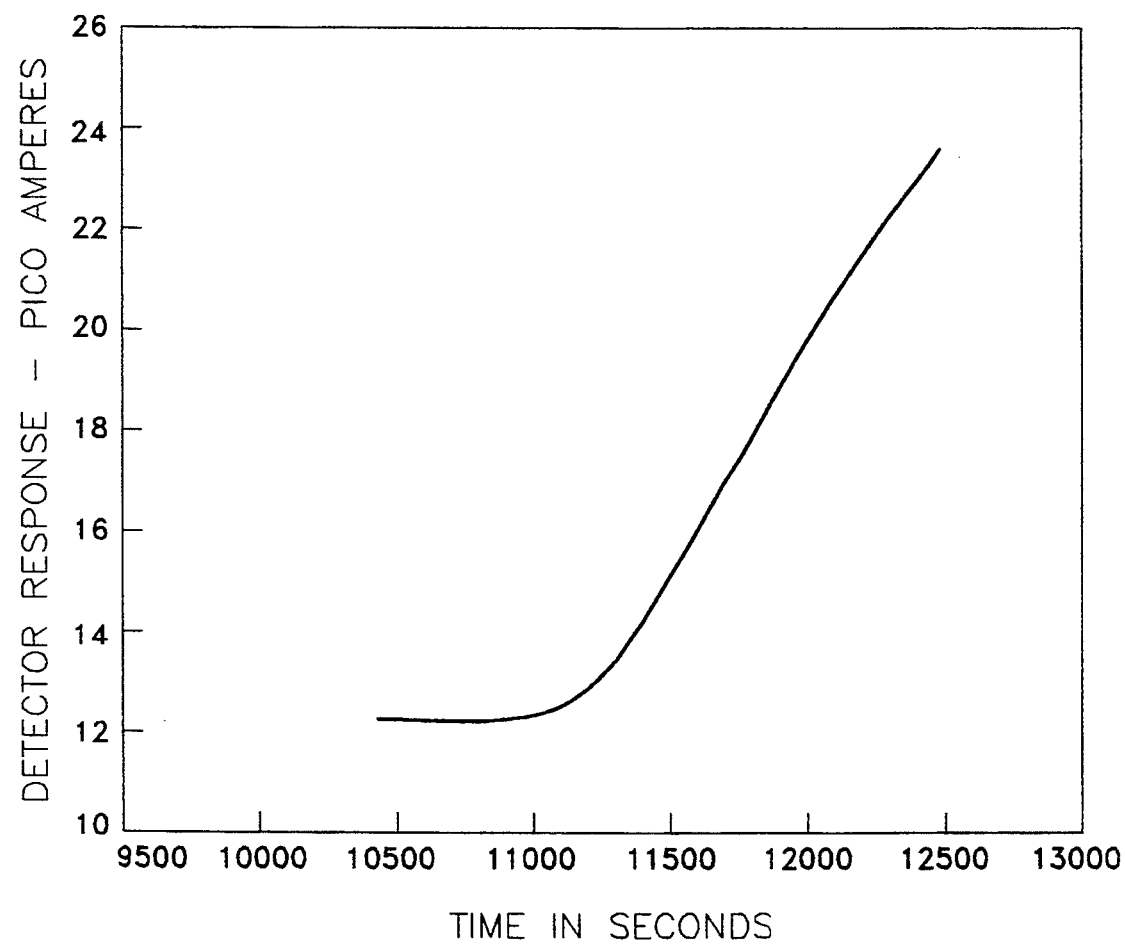
FIG. 5 illustrates a graph of amps vs. time for the permeation of D-limonene through polypropylene film at 50 deg. C according to the present invention.

FIG. 5 illustrates a graph of the flame ionization detector's analog signal vs. time in seconds (thousands). The curve illustrates the analog signal in picoamps as a response to the introduction of D-limonene test gas into the test cell and the permeation of the gas through polypropylene at 50 degrees C. The curve is a graph of both the theoretical response rate and the superimposed actual or observed response rate obtained by the present invention. The two curves are virtually identical, thereby allowing one to predict diffusion and permeation values with a degree of certainty equal to the identity shown in FIG. 5 between the actual and the theoretical response values. The y axis shows the detector response to D-limonene permeating through 1 mil thick polypropylene film at 50 degrees Centigrade. Thus, by the devices of the present invention, and as shown in FIG. 5, one can predict equilibrium long before equilibrium occurs. This is not possible by means of the devices of the prior art because those devices cannot make direct measurement of very low concentration of gas without expensive, cumbersome, or poorly effective additional concentration steps. This Figure also indicates the advantages of the devices of the present invention in precision and sensitivity for detection of gases having permeated through a barrier film, which advantages cannot be obtained by the devices of the prior art.

Figure 6:
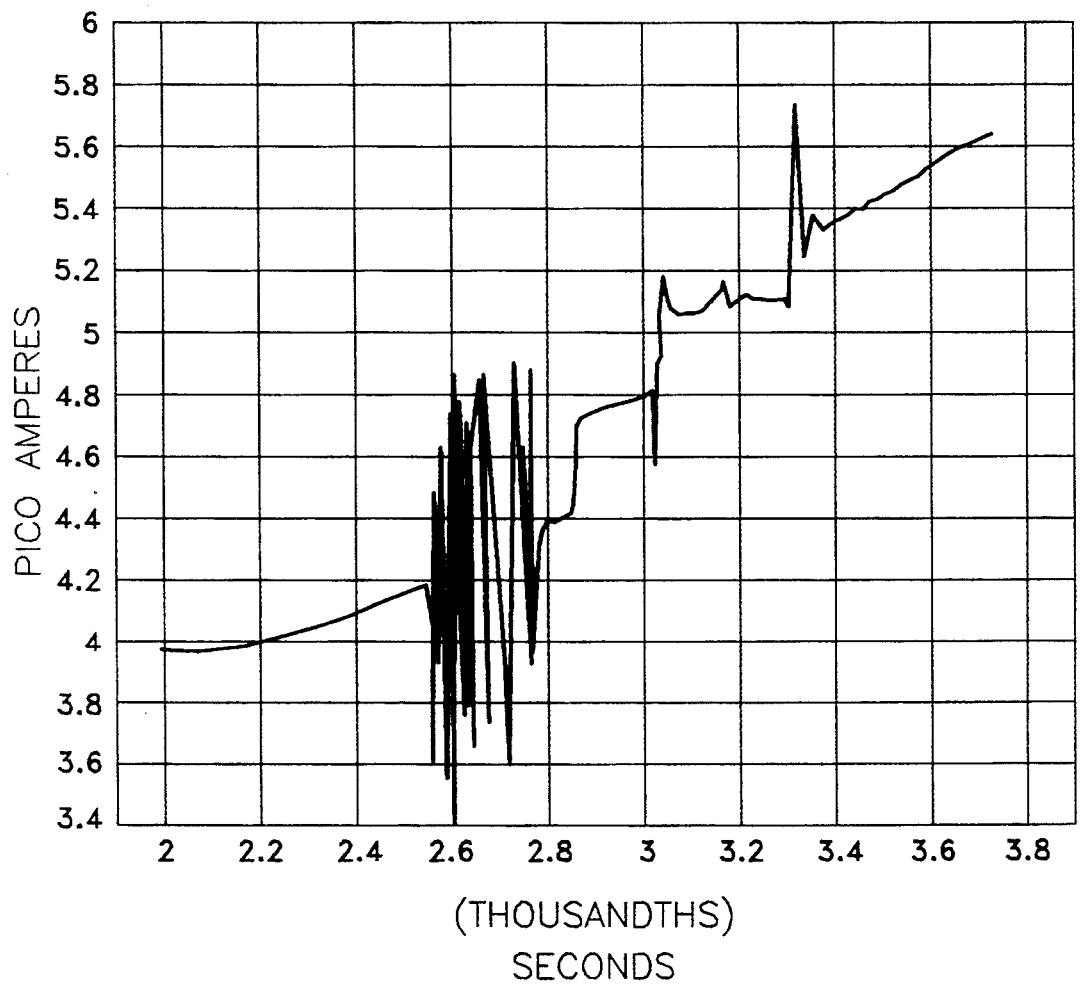
FIG. 6 illustrates a graph of the variation in detector signal response as a result of changes in several parameters.

FIG. 6 is a graph of the detector signal measured in picoamps vs. time as a result of several changes introduced to the system. At just before 2600 seconds, the detector sample size was reduced from 4000 to 1. At about 2800 seconds the detector sample size was increased back to 4000. At 2800 seconds, the nitrogen carrier gas flow rate was increased by 1 cc/minute causing a detector signal increase from 4.4 pico amperes to 4.8 pico amperes. At about 3000 seconds, the hydrogen gas flow rate was increased by 2 cc/minute causing a detector signal increase from 4.8 pico amperes to 5.1 pico amperes. At about 3200 seconds, the cell temperature was increased by 1 degree Centigrade. At about 3300 seconds, the cell temperature was increased another 4 degrees Centigrade. It should be noted that the effect of the flow rate changes and cell temperature changes would not be noticed without the detector signal averaging achieved by the present invention.

The following examples are meant to exemplify certain aspects of the invention and are in no way a limitation of the utility or design of the invention.

EXAMPLE

A test film of 100 gauge polypropylene polymer film was placed in the test cell device of the present invention. The temperature of the test cell was maintained at 50 degrees Centigrade by means of the thermocouples and cartridge heaters. A test gas of D-limonene at 100 ppm concentration was introduced into the first portion of the test cell. A carrier gas of nitrogen was introduced into the second portion of the test cell. A flame ionization detector, model 12-800 obtained from Gowmac, was used to collect the test gas swept by the carrier gas and measured at a sampling rate of 4000 samples per second. The flame ionization detector output analog signal was sent to a 386 Intel based computer equipped with an analog-to-digital converter and converted therein from an analog to digital signal and the signals were averaged to thereby reduce the background noise. In this manner, a detection level of 400 parts per billion by weight of D-limonene gas was detected in the early portion of the experiment, at 11,000 seconds. FIG. 5 illustrates the response obtained in this example.

While certain preferred embodiments of the present invention have been disclosed in detail, it is to be understood that various modifications may be adopted without departing from the spirit of the invention or scope of the following claims.

That which is claimed is:

1. An improvement in the method of detecting the passage of gas through a barrier film comprising the steps of;

a) exposing a first side of a film barrier to a test gas, whereby the test gas can permeate through the barrier film forming thereby a permeant gas;

b) exposing a second side of the barrier film to a carrier gas flow which mixes with the permeant gas;

c) collecting the carrier gas and permeant gas mixture in a detector able to detect the concentration of the permeant gas, whereby the detector can produce an analog signal which is proportional to the permeant gas concentration detected;

d) converting the analog signal from the detector to a digital signal; and e) averaging a plurality of digital signals, wherein said improvement comprises controlling the carrier gas flow to the detector with a pressure regulator and column end fittings possessing metallic frits.

2. The method of claim 1, wherein the metallic frits are sintered steel disks.

3. The method of claim 1, wherein the metallic frits have pore sizes ranging in diameter from 0.1 to about 25 microns.

4. An apparatus for detecting the passage of gas through a barrier film comprising;
   a) a barrier frit;
   b) a test cell for holding the barrier film whereby the test cell is divided into a first side and a second side by said barrier film;
   c) a means for supplying a test gas to the first side of the test cell;
   d) a means for supplying a carrier gas flow to the second side of the test cell;
   e) a detector for measuring test gas concentrations on said second side of the test cell, said detector able to send an analog output signal, wherein said analog signal is proportional to the test gas concentration detected;
   f) a computer to receive the analog output signal from the detector, convert the analog signal to a digital signal, and average the signals; and
   g) wherein the means for supplying the carrier gas flow comprises a pressure regulator and column end fittings possessing metallic frits.

5. The apparatus of claim 4, wherein the metallic frits are sintered steel disks.

6. The apparatus of claim 4, wherein the metallic frits have pore sizes ranging in diameter from 0.1 to about 25 microns.

* * * * *